de Patent [19]

United States Patent [19]

Clavenna et al.

[11] Patent Number: 4,530,934
[45] Date of Patent: Jul. 23, 1985

[54] PHARMACEUTICALLY ACTIVE URSOLIC ACID DERIVATIVE

[75] Inventors: Gaetano Clavenna, Rho; Carlo Farina, Valsolda; Mario Pinza, Corsico; Giorgio Pifféri, Milan, all of Italy

[73] Assignee: I.S.F. Spa, Milan, Italy

[21] Appl. No.: 511,761

[22] Filed: Jul. 25, 1983

[30] Foreign Application Priority Data

Jul. 26, 1982 [IT] Italy ................. 22566 A/82

[51] Int. Cl.$^3$ .............. A61K 31/225; C07C 69/40; C07C 67/08
[52] U.S. Cl. ................. 514/548; 514/925; 560/194
[58] Field of Search .............. 560/194; 424/313

[56] References Cited

U.S. PATENT DOCUMENTS

| | | | |
|---|---|---|---|
| 3,984,461 | 10/1976 | Pifferi | 560/194 |
| 4,000,186 | 12/1976 | Vanstone | 560/194 |
| 4,061,773 | 12/1977 | Chan | 424/313 |
| 4,448,788 | 5/1984 | Toyoshima et al. | 424/313 |

Primary Examiner—Natalie Trousof
Assistant Examiner—Vera C. Clarke
Attorney, Agent, or Firm—Stevens, Davis, Miller & Mosher

[57] ABSTRACT

There are described a new pharmaceutically active derivative of ursolic acid, 3β-(3-carboxypropionyloxy)ursa-9(11),12-dien-28-oic acid, which possesses activity as an anti-ulcer and anti-viral agent, pharmaceutically acceptable, non-toxic salts thereof, a method of preparing the same and compositions containing the same.

5 Claims, No Drawings

PHARMACEUTICALLY ACTIVE URSOLIC ACID DERIVATIVE

The present invention relates to a new pharmaceutically active derivative of ursa-9(11),12-dien-28-oic acid and the pharmaceutically acceptable, non-toxic salts thereof.

More particularly the present invention relates to 3β-(3-carboxypropionyloxy)ursa-9(11),12-dien-28-oic acid, which has been found to possess anti-ulcer and anti-viral activity practically free from any undesired side effects, a method of preparing the same and therapeutic compositions containing the same.

There is known in the art the existence of compounds having polycyclic structure and activity on ulcerative inflammation of the digestive system: among these, a derivative of glycyrrhetinic acid is the most interesting one, more precisely, the hydrogen succinate of glycyrrhetinic acid generally named carbenoxolone. Carbenoxolone possesses besides a pronounced anti-ulcer activity also a marked mineralcorticoid activity, which acts through an increased sodium and water retention and an increased potassium excretion. Such undesired mineralcorticoid activity makes the use of carbenoxolone not entirely suitable in therapy, at least in those cases where renal insufficiency and/or hypertension is present; besides it is known in the art that the concomitant administration of a diuretic potassium-sparing drug may cause the loss of the anti-ulcer activity of carbenoxolone itself.

The compound of the present invention is active in the treatment of ulcerative inflammations of the digestive system since it shows a marked cytoprotective action while is practically free, at the therapeutic effective dose level, from any mineralcorticoid activity. The compound of the invention, when compared with carbenoxolone at the same doses, was found to possess a similar anti-ulcer activity while it did not cause any significant sodium retention or potassium excretion.

ANTI-ULCER ACTIVITY

The anti-ulcer activity of the compounds under examination was evaluated using 3 models of induced gastric lesions in rats:

Stress-induced gastric lesions.—Female Sprague-Dawley rats fasted for 60 hours were used. The animals were immobilized in suitable restrictive containers and maintained at 4° C. for 2 hours. At the end of the test the incidence of the gastric lesions on the mucous membrane and their gravity was evaluated in the blind on the basis of the index obtained from the sum of the length expressed in mm of all the lesions.

The tested drugs, dissolved in distilled water, were administered p.o. at a dose of 100 mg/kg in 5 ml/kg, 15 minutes before exposure to stress. The results are shown in Table I.

Acetylsalicyclic acid-induced gastric lesions.—Male Sprague-Dawley rats fasted for 24 hours were used. The animals were treated with acetylsalicyclic acid at the dose of 200 mg/kg p.o. After 5 hours there were evaluated the incidence and the gravity of the lesions, in blind conditions, according to the method of Carmichael. The drugs under examination were administered concomitantly with the damaging agent at a dose of 5 ml/kg. The results are shown in Table I.

Absolute ethanol induced gastric lesions.—Male Sprague-Dawley rats fasted for 24 hours were used. The animals were treated orally with 1 ml of absolute ethanol. One hour later, the evaluation of the incidence and of the gravity of the lesions was performed in blind conditions according to an arbitrary scale from 0 to 5. The results are shown in Table I.

Mineralcorticoid activity was studied using male Sprague-Dawley rats. The animals, fasted for 24 hours, were given 5 ml p.o. of distilled water and 1 hour later 5 ml of phisiological solution and the drug under examination. The animals were then placed in metabolic cages for 5 hours. The parameters determined in the collected urine are given in Table II. The sodium and potassium concentration was evaluated by flame photometry.

The compound of the invention as well as the pharmaceutically acceptable non-toxic salts thereof, can be mixed with suitable known inert solid or liquid carriers in order to be pharmaceutically administered to humans in the form of tablets, capsules, granules, solutions, emulsions and the like. Suitable carriers are those generally used in the art such as lactose, mannitol, aluminum hydroxide, magnesium trisilicate, skimmed milk, and the like. The dosage for treating patients suffering from ulcerative inflammation of the digestive system is between 100 and 300 mg daily for an adult weighing approximately 60 kg.

TABLE I

| Anti-Ulcer Activity in Rats | | | |
|---|---|---|---|
| Lesions Induced By: | Treatment 100 mg/kg os | Number of Rats | Lesion Index (Mean + s.e.) |
| Stress | Control | 14 | 5.07 ± 1.47 |
| | Carbenoxolone | 15 | 2.40 ± 0.58* |
| | Disodium salt of 3β-(3-carboxypropionyloxy)ursa-9(11),12-dien-28-oic acid | 15 | 1.53 ± 0.53* |
| Absolute ethanol | Control | 8 | 2.37 ± 0.49 |
| | Carbenoxolone | 8 | 0.37 ± 0.18** |
| | Disodium salt of 3β-(3-carboxypropionyloxy)ursa-9(11),12-dien-28-oic acid | 8 | 0.62 ± 0.18** |
| Aspirin | Control | 15 | 27.50 ± 6.35 |
| | Carbenoxolone | 15 | 9.60 ± 2.44* |
| | Disodium salt of 3β-(3-carboxypropionyloxy)ursa-9(11),12-dien-28-oic acid | 15 | 11.30 ± 2.32* |

*$P < 0.05$
**$P < 0.01$
compared with control group (Dunnett's test)

TABLE II

| Treatment | Mineralcorticoid Activity (Diuresis in Rats) | | | | | | |
|---|---|---|---|---|---|---|---|
| | Dose mg/kg os route | urinary excretion % change compared with control group | | | | | |
| | | Volume | Na+ | | K+ | | Na+/K+ |
| | | | conc./l | 5 h excr. | conc./l | 5 h excr. | |
| Carbenoxolone | 10 | −12 | −13 | −23 | +37 | +22 | −35* |
| | 30 | −15 | −13 | −26* | +57* | +35* | −44** |
| | 100 | −33** | −33** | −54** | +150** | +66** | −73** |
| Disodium salt of 3β-(3-Carboxypropioniloxy)ursa-9(11),12-dien-28-oic acid | 30 | −13 | +30 | +13 | +21 | +3 | +8 |
| | 100 | −22* | +35* | +8 | +34 | +4 | +9 |

*$P < 0.05$
**$P < 0.01$
compared with control group (Dunnett's test)

The compound of the present invention is obtained by succinylation of 3β-hydroxy-ursa-9(11),12-dien-28-oic acid according to the known method. The following Examples are given for the purpose of better illustrating the present invention without limiting the same.

EXAMPLE 1

Disodium salt of 3β-(3-carboxypropionyloxy)ursa-9(11),12-dien-28-oic acid

Grams 60 of 3β-hydroxy-ursa-12-en-28-oic acid and 12 g sodium acetate are treated with 480 ml glacial acetic acid and 120 ml acetic anhydride and refluxed until the complete dissolution. The solution is kept under such conditions for 2 hours; then, to it are added 2 l water with stirring for 2 hours. The precipitate is filtered off, washed 3 times with 100 ml water, then dried under vacuo until constant weight is reached to give 64.5 g 3β-acetoxy-ursa-12-en-28-oic acid melting at 158°–180° C.

Grams 64 of 3β-acetoxy-ursa-12-en-28-oic acid and 30 g N-bromosuccinimide in 1.5 l carbon tetrachloride are refluxed under stirring for 3 hours and a half. It is filtered and the residue obtained is washed twice with 20 ml methylene chloride. The filtrate is then washed 3 times with 300 ml of a saturated solution of sodium metabisulphite and 3 times with a saturated ammonium sulphate solution. It is made anhydrous over magnesium sulphate, evaporated under vacuo and the residue obtained is taken up with 450 ml of 96% ethyl alcohol, then there is added to the solution 450 ml of 30% sodium hydroxide, and the mixture is refluxed for 2 hours. About 350 ml of ethyl alcohol are distilled under vacuo, then it is acidified to Red Congo with 20% sulphuric acid. The reaction mixture is filtered under vacuo, the residue obtained is washed twice with 100 ml water, dried under vacuo until constant weight is reached to give 58 g 3β-hydroxy-ursa-9(11),12-dien-28-oic acid melting at 200°–230° C.

A solution consisting of 58 g 3β-hydroxy-ursa-9(11),12-dien-28-oic acid, 64 g succinic anhydride and 450 ml pyridine is refluxed for about 18 hours, then it is added slowly, while stirring, to 450 ml of 96% sulphuric acid in 5 l ice. The so-obtained precipitate is collected under vacuo, washed twice with 200 ml water, dried until constant weight is reached, then chromatographed over silica (eluent: methylene chloride/tetrahydrofuran, 95/5), thus obtaining 30 g 3β-(3-carboxypropionyloxy)ursa-9(11),12-dien-28-oic acid melting at 219°–223° C.

A solution of 30 g 3β-(3-carboxypropionyloxy)ursa-9(11),12-dien-28-oic acid in 1200 ml tetrahydrofuran is treated dropwise under stirring with 108 ml N methanolic sodium hydroxide. It is stirred for a further 10 minutes, then the precipitate obtained is filtered under vacuo, washed twice with 50 ml tetrahydrofuran, and dried until constant weight to give 30.6 g disodium salt of 3β-(3-carboxypropionyloxy)ursa-9(11),12-dien-28-oic acid melting at 328°–331° C. (with decomposition).

EXAMPLE 2

Disodium salt of 3β-(3-carboxypropionyloxy)ursa-9(11),12-dien-28-oic acid

A solution containing 58 g 3β-hydroxy-ursa-9(11),12-dien-28-oic acid, 126 g succinic anhydride and 10 g 4-dimethylaminopyridine in 1800 ml pyridine is stirred at ambient temperature for 48 hours, then heated to 60° C. for 3 hours. The reaction mixture is poured into 20% sulphuric acid, the precipitate obtained is collected under vacuo, chromatographed over silica eluting with ethyl acetate and there are thus obtained 48.5 g 3β-(3-carboxypropionyloxy)ursa-9(11),12-dien-28-oic acid melting at 218°–222° C.

A solution of 48.5 g 3β-(3-carboxypropionyloxy)ursa-9(11),12-dien-28-oic acid in 600 ml tetrahydrofuran and 2400 ml acetone is treated dropwise at ambient temperature, while stirring, with 174.6 ml N methanolic sodium hydroxide. The precipitate is filtered under vacuo, triturated with acetone, filtered again under vacuo to give 47.3 g disodium salt of 3β-(3-carboxypropionyloxy)ursa-9(11),12-dien-28-oic acid, which is identical to the compound obtained in Example 1.

EXAMPLE 3

Granules were prepared by mixing 50 mg disodium salt of 3β-(3-carboxypropionyloxy)ursa-9(11),12-dien-28-oic acid with 216 mg lactose, wetting with purified water, passing through a screw and drying under air stream. It is then mixed with granules containing 200 mg aluminum hydroxide, 50 mg magnesium trisilicate and 274 mg mannitol. Then it is mixed with 810 mg of granules of skimmed milk.

EXAMPLE 4

Capsules were prepared by mixing 50 mg disodium salt of 3β-(3-carboxypropionyloxy)ursa-9(11),12-dien-28-oic acid, 50 mg aluminum hydroxide, 50 mg magnesium trisilicate, 345 mg of lactose and 5 mg of magnesium stearate and then filling in hard gelatin capsules of 0 size.

What is claimed is:

1. 3β-(3-Carboxypropionyloxy)ursa-9(11),12-dien-28-oic acid and the pharmaceutically acceptable, non-toxic salts thereof.

2. Disodium salt of 3β-(3-carboxypropionyloxy)ursa-9(11),12-dien-28-oic acid.

3. Process for the preparation of 3β-(3-carboxypropionyloxy)ursa-9(11),12-dien-28-oic acid and the pharmaceutically acceptable, non-toxic salts thereof, comprising:
   (a) succinylating 3β-hydroxy-ursa-9(11),12-dien-28-oic acid in the presence of a catalytic amount of 4-dimethylaminopyridine;
   (b) stirring the reaction mixture of step (a) at ambient temperature;
   (c) heating and precipitating the product of step (b) with a dilute acid; and
   (d) optionally converting the so obtained emisuccinate into a suitable pharmaceutically acceptable non-toxic salt.

4. A therapeutic composition for the treatment of ulcers comprising an antiulcerogenically effective amount of a compound according to claim 1 in admixture with a pharmaceutically acceptable excipient.

5. A therapeutic composition for the treatment of ulcers comprising an antiulcerogenically effective amount of a compound according to claim 2 in admixture with a pharmaceutically acceptable excipient.

* * * * *